(12) United States Patent
Okuda et al.

(10) Patent No.: US 7,745,198 B2
(45) Date of Patent: Jun. 29, 2010

(54) METHOD OF PRODUCING MACROLIDE COMPOUND

(75) Inventors: Akifumi Okuda, Ibaraki (JP); Satoshi Yamamoto, Ibaraki (JP); Takashi Sakai, Ibaraki (JP); Susumu Takeda, Shizuoka (JP); Takashi Nakashima, Kanagawa (JP); Katsura Kaneko, Shizuoka (JP); Tomohiro Sameshima, Shizouka (JP); Taira Kato, Shizuoka (JP); Naoto Kawamura, Kanagawa (JP)

(73) Assignees: Mercian Corporation, Tokyo (JP); Eisai R&D Management Co., Ltd., Tokyo (JP)

( * ) Notice: Subject to any disclaimer, the term of this patent is extended or adjusted under 35 U.S.C. 154(b) by 840 days.

(21) Appl. No.: 10/532,412

(22) PCT Filed: Nov. 27, 2003

(86) PCT No.: PCT/JP03/15170

§ 371 (c)(1),
(2), (4) Date: Apr. 22, 2005

(87) PCT Pub. No.: WO2004/050890

PCT Pub. Date: Jun. 17, 2004

(65) Prior Publication Data

US 2006/0141589 A1   Jun. 29, 2006

(30) Foreign Application Priority Data

Nov. 29, 2002   (JP) ............................. 2002-346796

(51) Int. Cl.
*C12N 1/20*   (2006.01)
*A01N 43/02*   (2006.01)

(52) U.S. Cl. .................................. 435/252.3; 514/450
(58) Field of Classification Search ............... 436/252.3
See application file for complete search history.

(56) References Cited

U.S. PATENT DOCUMENTS

| | | | |
|---|---|---|---|
| 6,712,617 B2 | 3/2004 | Detmar et al. | |
| 7,026,352 B1 * | 4/2006 | Mizui et al. | 514/450 |
| 7,256,178 B2 * | 8/2007 | Kotake et al. | 514/28 |
| 2008/0021226 A1 | 1/2008 | Kanada et al. | |

FOREIGN PATENT DOCUMENTS

| | | |
|---|---|---|
| JP | 4-352783 A | 12/1992 |
| WO | WO-00/75126 A1 | 12/2000 |
| WO | WO-02/12533 A2 | 2/2002 |
| WO | WO-02/060890 A1 | 8/2002 |
| WO | WO-03/099813 A1 | 12/2003 |

OTHER PUBLICATIONS

Seki-Asano et al. ( The Journal of Antibiotics, vol. 47, No. 12, pp. 1395-1401, 1994).*

Ronald A. Lemahieu et al.; The Journal of Antibiotics, Jul. 1976, vol. 29, No. 7, pp. 728-734.
Roberto Spagnoli et al.; The Journal of Antibiotics, Apr. 1983, vol. 36, No. 4, pp. 365-375.
A. Anadon; Research in Veterinary Science, Jun. 1999, vol. 66, No. 3, pp. 197-203.
D.J. Farrell et al.; Journal of Antimicrobial Chemotherapy, Sep. 2002, vol. 50, Suppl., pp. 39-47.
Sakai et al., "Shinki ko-shuyo kassei busshitsu pladienolide ni kansuru kenkyu (1)-shinki 12-inkan macrolide pladeienolide B no tanri to kozo", Japan Society for Bioscience, Biotechnology, and Agrochemistry, Taikai Koen Yoshishu, Mar. 2003, p. 123.

(Continued)

*Primary Examiner*—Robert Mondesi
*Assistant Examiner*—Khatol Shahnan-Shah
(74) *Attorney, Agent, or Firm*—Birch, Stewart, Kolasch & Birch, LLP

(57) ABSTRACT

The present invention provides a novel method of producing the 12-membered ring macrolide compound 11107D having an antitumor activity by biological transformation. Starting material which is the 12-membered ring macrolide compound 11107B represented by the formula (I) is incubated in the presence of a strain belonging to the genus *Mortierella*, the genus *Streptomyces* or the family Micromonosporaceae (for example, *Streptomyces* sp. AB-1704 strain (FERM BP-8551)), each of which has the ability of transforming the 12-membered ring macrolide compound 11107B into a 11107D substance represented by the formula (II), or a preparation of its cultured myceha and oxygen, and then 11107D substance which is a target material is collected from the treating solution.

3 Claims, No Drawings

OTHER PUBLICATIONS

Akifumi et al., "Shinki ko-shuyo kassei busshitsu pladienolide ni kansuru kenkyu (2) VEGF sansei yokusei kassei o shihyo to shita pladienolide-rui no kozo kassei sokan", Japan Society for Bioscience, Biotechnology, and Agrochemistry, Taikai Koen Yoshishu, Mar. 2003, p. 124.

Keiji et al., "Shinki ko-shuyo kassei busshitsu pladienolide ni kansuru kenkyu (3)-pladienolide-rui no yakuri kassei (in vitro, in vivo)", Japan Society for Bioscience, Biotechnology, and Agrochemistry, Taikai Koen Yoshishu, Mar. 2003, p. 124.

Proceedings for 2003 Annual Meeting of Japan Society for Bioscience, Biotechnology, and Agrochemistry, pp. 123-124, (2003).

Ryuichi Morishita. "Recent Progress in Gene Therapy for Cardiovascular Disease", Circ Journal, vol. 66, pp. 1077-1086, 2002.

Moon-Seok Cha, "Endogenous Production of Nitric Oxide by vascular Endothelial Growth Factor Down-Regulates Proliferation of Choriocarcinoma Cells", Biochemical and Biophysical Research Communications, vol. 282, pp. 1061-1066, 2001.

Bestmann, Hans Jurgen. Synthesis, 1989, vol. 6, pp. 419-423.

Bestmann, Jans Jurgen. Angew. Chem., 1983, vol. 95, No. 10, pp. 810-811.

Furstner, Alois et al. Efficient Total Syntheses of Resin Glycosides and Analogues by Ring-Closing Olefin Metathesis, J. Am. Chem. Soc., 1999, vol. 121, pp. 7814-7821.

Gunawardana, Geewananda, et al. J. Am. Chem. Soc. 1999, vol. 121, pp. 6092-6093.

Rohr, Jurgen. Angew Chem. Int. Ed., 2000, vol. 39, No. 16, pp. 2847-2849.

Kobayashi, Jun'ichi et al. Tetrahedron Letters, 1996, vol. 37, No. 9, pp. 1449-1450.

Hamberg, Mats. Lipids, 2000, vol. 35, No. 4, pp. 353-363.

Hamberg, Mats. Chem. Phys. Lipids, 1988, vol. 46, No. 4, pp. 235-243.

* cited by examiner

METHOD OF PRODUCING MACROLIDE COMPOUND

TECHNICAL FIELD

The present invention relates to a method of producing the 12-membered ring macrolide compound 11107D having an antitumor activity by biological transformation and to a novel strain used for the production.

PRIOR ART

The 12-membered ring macrolide compound 11107D is a 12-membered ring macrolide compound having an excellent antitumor activity and was discovered together with a 11107B substance from a culture product of a *Streptomyces* sp. Mer-11107 strain (see WO-A02/060890). The 11107D substance corresponds to a 16-position hydroxide body of the 11107B. The productivity of the 11107D substance is inferior to that of the 11107B substance and it has been therefore desired to establish an efficient production method.

DISCLOSURE OF THE INVENTION

The purpose of the present invention is to provide a novel method of producing the macrolide compound 11107D by using the macrolide compound 11107B as starting material by a biological transformation method.

The inventors of the present invention have made a trial to select microorganisms capable of transforming the 16-position hydrogen atom to hydroxyl group of the macrolide compound 11107B by screening from a wide range of microorganism groups to solve the above problem, and as a result, found that a strain belonging to the genus *Mortierella* classified into the filamentous fungi, a strain belonging to the genus *Streptomyces* classified into actinomycetes and a strain belonging to the family Micromonosporaceae likewise classified into actinomycetes have the above-mentioned transforming function, to complete the present invention.

Accordingly, the present invention relates to the following (1) to (3).
(1) A method of producing the macrolide compound 11107D represented by the formula (II):

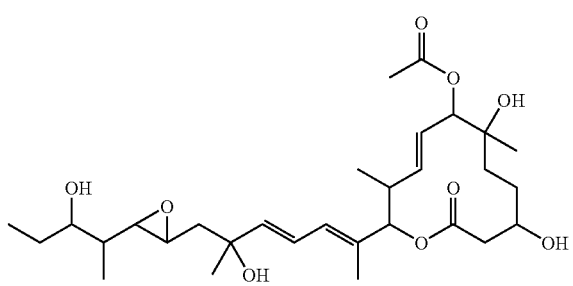

(II)

wherein the macrolide compound 11107D is produced from the macrolide compound 11107B represented by the formula (I):

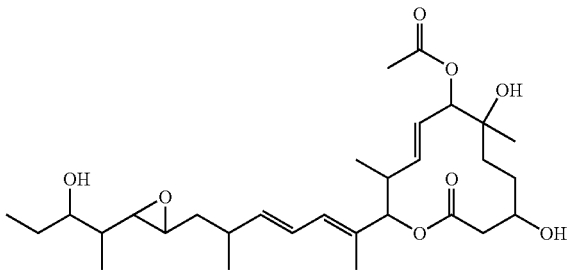

(I)

by a biological transformation method, which comprises the following processes (A) and (B):

(A) a process of incubating the macrolide compound 11107B represented by the formula (I) in the presence of a strain having an ability of conducting the above-mentioned biological transformation method and belonging to the genus *Mortierella*, the genus *Streptomyces* or the family Micromonosporaceae or a preparation of its cultured mycelia; and (B) a process of collecting the macrolide compound 11107D represented by the formula (II) from the incubated solution obtained in the step (A).

(2) The production method according to the above (1), wherein the strain belonging to the genus *Mortierella* is *Mortierella* sp. F-1529 strain (FERM BP-8547) or F-1530 strain (FERM BP-8548)

(3) The production method according to the above (1), wherein the strain belonging to the genus *Streptomyces* is *Streptomyces*sp. AB-1704 strain (FERM BP-8551), A-1544 strain (FERM BP-8446) or A-1545 strain (FERM BP-8447).

(4) The production method according to the above (1), wherein the strain belonging to the family Micromonosporaceae is AB-1896 strain (FERM BP-8550).

(5) *Streptomyces* sp. AB-1704 strain (FERM BP-8551) having the ability of transforming the macrolide compound 11107B represented by the formula (I) into the macrolide compound 11107D represented by the formula (II).

(6) *Mortierella* sp. F-1529strain (FERM BP-8547) or F-1530 strain (FERM BP-8548) having the ability of transforming the macrolide compound 11107B represented by the formula (I) into the macrolide compound 11107D represented by the formula (II).

(7) AB-1896 strain (FERM BP-8550) having the ability of transforming the macrolide compound 11107B represented by the above formula (I) into the macrolide compound 11107D represented by the above formula (II).

DETAILED DESCRIPTION OF THE INVENTION

In the biological transformation method of the present invention, any microorganisms belonging to the genus *Mortierella*, the genus *Streptomyces* or the family Micromonosporaceae may be used regardless of the type of species and strain insofar as it has the ability to transform the macrolide compound 11107B represented by the above formula (I) into the macrolide compound 11107D represented by the above formula (II). However, preferable examples of the microorganisms may include the *Mortierella* sp. F-1529 strain and F-1530 strain belonging to the genus *Mortierella*, the *Streptomyces* sp. AB-1704 strain, A-1544 strain and A-1545 strain belonging to the genus *Streptomyces* and the AB-1896 strain belonging to the family Micromonosporaceae, each has isolated from the soil.

The Mer-11107 strain was deposited as FERM P-18144 at the National Institute of Bioscience and Human-Technology Agency of Industrial Science and Technology (1-3, Higashi 1-chome Tsukuba-shi, Ibaraki-ken 305-8566 Japan), now reorganized to International Deposit FERM BP-7812 at International Patent Organism Depositary (IPOD) National Institute of Advanced Industrial Science and Technology (Tsukuba Central 6,1-1, Higashi 1-Chome, Tsukuba-shi, Ibaraki-ken 305-8566 Japan), as of Dec. 19, 2000, and then transferred to International Deposit FERM BP-7812 at International Patent Organism Depositary (IPOD) National Institute of Advanced Industrial Science and Technology (Tsukuba Central 6, 1-1, Higashi 1-Chome, Tsukuba-shi, Ibaraki-ken 305-8566 Japan) as of Nov. 27, 2001.

The *Mortierella* sp. F-1529 strain was internationally deposited at International Patent Organism Depositary National Institute of Advanced Industrial Science and Technology (Tsukuba Central 6, 1-1, Higashi 1-Chome, Tsukuba-shi, Ibaraki-ken 305-8566 Japan) as of Nov. 12, 2003 as FERM BP-8547. Also, the *Mortierella* sp. F-1530 strain was internationally deposited at International Patent Organism Depositary National Institute of Advanced Industrial Science and Technology (Tsukuba Central 6, 1-1, Higashi 1-Chome, Tsukuba-shi, Ibaraki-ken 305-8566 Japan) as of Nov. 12, 2003 as FERM BP-8548.

The *Streptomyces* sp. AB-1704 strain was deposited at International Patent Organism Depositary National Institute of Advanced Industrial Science and Technology (Tsukuba Central 6, 1-1, Higashi 1-Chome, Tsukuba-shi, Ibaraki-ken 305-8566 Japan) as FERM P-18999 as of Sep. 5, 2002, and then transferred to International Deposit FERM BP-8551 as of Nov. 12, 2003, at International Patent Organism Depositary (IPOD) National Institute of Advanced Industrial Science and Technology (Tsukuba Central 6, 1-1, Higashi 1-Chome, Tsukuba-shi, Ibaraki-ken 305-8566 Japan). Also, the A-1544 strain and A-1545 strain were deposited at International Patent Organism Depositary National Institute of Advanced Industrial Science and Technology (Tsukuba Central 6, 1-1, Higashi 1-Chome, Tsukuba-shi, Ibaraki-ken 305-8566 Japan) as FERM P-18943 and FERM P-18944 as of Jul. 23, 2002, and then transferred to International Deposit FERM BP-8446 and FERM BP-8447 as of Jul. 30, 2003 respectively, at International Patent Organism Depositary (IPOD) National Institute of Advanced Industrial Science and Technology (Tsukuba Central 6, 1-1, Higashi 1-Chome, Tsukuba-shi, Ibaraki-ken 305-8566 Japan).

The AB-1896 strain belonging to the family Micromonosporaceae was internationally deposited at International Patent Organism Depositary National Institute of Advanced Industrial Science and Technology (Tsukuba Central 6, 1-1, Higashi 1-Chome, Tsukuba-shi, Ibaraki-ken 305-8566 Japan) as FERM-BP 8550 as of Nov. 12, 2003.

The taxonomical properties of the above strains are as follows.

(The Taxonomical Properties of the F-1529 Strain)
(1) Morphological Characteristics On each plate of oatmeal agar (hereinafter abbreviated as OA as the case may be), malt agar (2% malt extract+1.5% agar: hereinafter abbreviated as MEA as the case may be) and potato dextrose agar (hereinafter abbreviated as PDA as the case may be), the colony had a floccose form and the color of the hyphae was white, exhibiting white (1A-1) tone. As to the growth when the strain was cultured at 25° C. for one week, the colonies reached 75 mm in diameter on the OA plate, 75 to 80 mm in diameter on the MEA plate and 75 to 80 mm in diameter on the PDA plate. The colony had a zonate shape. Neither backside coloring nor the production of soluble pigment was not observed. The the color tone was described according to "Methuen Handbook of Colour (Kornerup & Wanscher, 1978)".

As a result of the observation using an optical microscope, the vegetative hyphae were colorless, had a smooth surface, were provided with no septum and had a width of 4 to 5 μm. A swelled structure like that of a thick wall spore having a spherical form and a size of about 26.5 to 33 μm was observed in a part of the hypahe. In the culture media to be subjected to the test, any structure that seems to be a genital organ was not formed even by culturing for a term not exceeding 3 weeks.

(2) 18S rRNA Gene Analysis

A mycelia of the F-1529 strain cultured on an agar plate was subjected to DNA extraction using Fast Prep FP120 (manufactured by Q-BIO gene) and Fast DNA Kit (manufactured by Q-BIO gene). PCR was practiced using puRetaq Ready-To-Go PCR beads (manufactured by Amersham Biosciences) and PCR primers NS1 and NS8 shown in Tables 1 and 2. The PCR products were refined using QIAquick PCR Purification Kit (manufactured by QIAGEN) and then treated with ABI Prism BigDye Terminator Kit (manufactured by Applied Biosystems). As the sequencing primers NS1, NS2, NS3, NS4, NS5, NS6, NS7 and NS8 shown in Tables 1 and 2 were used. The reaction products were refined using a Dye EX2.0 Spin Kit (manufactured by QIAGEN) and subjected to sequence analysis using an ABI PRISM 3100 Genetic Analyzer (manufactured by Applied Biosystems). Then, the sequenced fragments were combined together by using an Auto Assembler (manufactured by Applied Biosystems) to obtain the full length nucleotide sequence.

TABLE 1

Primers used to determine nucleotide sequence of 18s rRNA gene (forward direction)

| SEQ ID NO: | Name | Sequence |
|---|---|---|
| 1 | NS1 | 5'-gtagtcatatgcttgtct-3' |
| 2 | NS3 | 5'-gcaagtctggtgccagcagcc-3' |
| 3 | NS5 | 5'-aacttaaaggaattgacggaag-3' |
| 4 | NS7 | 5'-gaggcaataacaggtctgtgatg-3' |

TABLE 2

Primers used to determine nucleotide sequence of 18s rRNA gene (reverse direction)

| SEQ ID NO: | Name | Sequence |
|---|---|---|
| 5 | NS2 | 5'-cgttcagaccacggtcgtcgg-3' |
| 6 | NS4 | 5'-ttgaatttccttaactgccttc-3' |
| 7 | NS6 | 5'-ctccgttattgtccagacactac-3' |
| 8 | NS8 | 5'-aggcatccacttggacgcct-3' |

Thus obtained 18S rRNA gene of the strain has a nucleotide sequence described in Sequence No. 9.

The DNA sequence of a known strain was obtained from Japan DNA Data Bank to examine the homology of the 18S rRNA genes. As a result, this 18S rRNA gene had 99% (upstream 803 bases) homology with the 18S rRNA gene of *Mortierella* hyalina (GenBank, accession no. AY157493), 98% (full length) homology with the 18S rRNA gene of Mortierella chiamydospora (GenBank accession No. AF157143) and 98% (full length) homology with the 18S rRNA gene of Mortierella multidivaricata (GenBank accession No. AF157144).

From the above mycological properties, the inventors of the present invention determined that this strain belongs to the genus *Mortierella*.

Taxonomical Properties of the F-1530 Strain (1) Morphological Characteristics

On each plate of oatmeal agar, malt agar and potato dextrose agar, the colony had a cottony form and the color of the hyphae was white, exhibiting white (1A-1) tone. As to the growth when the strain was cultured at 25° C. for one week, the strain reached 80 to 85 mm in diameter on the OA plate, 85 mm in diameter on the MEA plate and 85 mm in diameter on the PDA plate. The colony had a zonate shape. Neither backside coloring nor the production of soluble pigment was not observed. The color tone was described according to "Methuen Handbook of Colour (Kornerup & Wanscher, 1978)).

As a result of observation using an optical microscope, vegetative hyphae were colorless, had a smooth surface, were provided with no septum and had a width of 2.5 to 5 μm. As welled structure like that of a thick wall spore, having a spherical form and a size of about 10 μm is observed in a part of the hyphae. In the culture media to be subjected to the test, any structure that seems to be a genital organ was not formed even by culturing for a term not exceeding 3 weeks.

(2) 18S rRNA Gene Analysis

The 18S rRNA gene of the F-1530 strain was analyzed in the same manner as in the case of the F-1529 strain. Thus obtained 18S rRNA gene of the F-1530 strain had a nucleotide sequence described in Sequence No. 10.

The DNA sequence of a known strain was obtained from Japan DNA Data Bank to examine the homology of the 18S rRNA genes. As a result, this 18S rRNA gene had 100% (upstream 803 bases) homology with the 18S rRNA gene of *Mortierella* hyalina (GenBank, accession no. AY157493), 98% (full length) homology with the 18S rRNA gene of Mortierella chlamydospora (GenBank accession No. AFI 57143) and 98% (full length) homology with the 18S rRNA gene of mortierella multidivaricata (GenBank accession No. AF 157144).

From the above-mentioned microbial characteristics, the present inventors determined that the present strain belongs to the genus *Mortierella*.

(The Taxonomical Properties of the AB-1704 Strain)

(1) Morphological Characteristics

Rectiflexibiles type aerial hyphae were extended from vegetative hyphae in this strain. Spore chains consisting of about 20 to 50 of cylindrical spores were formed at the end of the matured aerial hyphae. The size of the spores was about 0.6 to 0.8×1.0 to 1.1 μm, the surface of the spores was smooth, and specific organs such as sporangium, sclerotium and flagellum were not observed.

(2) Cultural Characteristics on Various Media

Cultural characteristics of the strain after incubation at 28° C. for two weeks on various media are shown in Table 3. The color tone is described by the color names and codes which are shown in the parentheses of Tresner's Color wheels.

TABLE 3

| Medium | Growth | Aerial hyphae | Color of vegetative hyphae | Soluble pigment |
|---|---|---|---|---|
| Yeast extract - malt extract agar (ISP-2) | Good | Thick Ivory (2db) | Nude tan (4gc) | None |
| Oatmeal agar (ISP-3) | Good | Abundant Ivory (2db) | Light melon yellow (3ea) | None |
| Inorganic salts - starch agar (ISP-4) | Good | Thick Putty–Ivory (1½ec–2db) | Cork tan (4ie) | None |
| Glycerol - asparagine agar (ISP-5) | Good | Thick Parchment (1½db) | Nude tan (4gc) | None |
| Peptone-yeast extract - iron agar (ISP-6) | Good | Abundant White (a) | Light melon yellow (3ea) | None |
| Tyrosine agar (ISP-7) | Good | Thick Ivory (2db) | Nude tan (4gc) | None |

(3) Utilization of Various Carbon Sources

Various carbon sources were added to Pridham-Gottlieb agar and cultured at 28° C. for 2 weeks. The growth of the strain is shown in Table 4.

TABLE 4

| D-glucose | + | inositol | – |
| L-arabinose | ± | L-rhamnose | + |
| D-xylose | + | D-mannitol | + |
| D-fructose | + | raffinose | – |
| sucrose | ± | | |

(+: positive, ±: slightly positive, –: negative)

(4) Various Physiological Properties

Various physiological properties of the present strain are as follows.

(a) Range of growth temperature (yeast extract-malt extract agar, incubation for 2 weeks) 5° C. to 33° C.
(b) Range of optimum growth temperature (yeast extract-malt extract agar, incubation for 2 weeks) 15° C. to 33° C.
(c) Liquefaction of gelatin (glucose-peptone-gelatin medium) positive
(d) Coagulation of milk (skim milk medium) positive
(e) Peptonization of milk (skim milk medium) positive
(f) Hydrolysis of starch (inorganic salts-starch agar) positive
(g) Formation of melanoid pigment (peptone-yeast extract-iron agar) negative, (tyrosine agar) negative
(h) Production of hydrogen sulfide (peptone-yeast extract-iron agar) negative
(i) Reduction of nitrate (broth containing 0.1% potassium nitrate) positive
(j) Sodium chloride tolerance (yeast extract-malt extract agar, incubation for 2 weeks) grown at a salt content of 7% or less (5) Chemotaxonomy LL-diaminopimelic acid was detected from the cell wall of the present strain.

From the above-mentioned microbial characteristics, the present inventors determined that the present strain belongs to the genus Streptomyces.

(The Taxonomical Properties of A-1544 Strain)

(1) Morphological Characteristics

Spira type aerial hyphae were extended from vegetative hyphae in this strain. Spore chains consisting of about 10 to 20 of cylindrical spores were formed at the end of the matured aerial hyphae. The size of the spores was about 1.0×1.2 to 1.94 μm, the surface of the spores was spiny, and specific organs such as sporangium, sclerotium and flagellum were not observed.

(2) Cultural Characteristics on Various Media

Cultural characteristics of the strain after incubation at 28° C. for two weeks on various media are shown in Table 5. The color tone is described by the color names and codes which are shown in the parentheses of Tresner's Color wheels.

TABLE 5

| Medium | Growth | Aerial hyphae | Color of vegetative hyphae | Soluble pigment |
|---|---|---|---|---|
| Yeast extract - malt extract agar (ISP-2) | Good | Thick Silver gray (3fe) | Light melon yellow (3ea) | None |
| Oatmeal agar (ISP-3) | Good | Abundant Light gray–Silver gray (d–3fe) | Light melon yellow (3ea) | None |
| Inorganic salts - starch agar (ISP-4) | Good | Abundant Silver gray (3fe) | Light melon yellow (3ea) | None |
| Glycerol - asparagine agar (ISP-5) | Good | Abundant Ashes (5fe) | Light melon yellow (3ea) | None |
| Peptone-yeast extract - iron agar (ISP-6) | Good | None | Light melon yellow (3ea) | Pale blackish brown |
| Tyrosine agar (ISP-7) | Good | Abundant Covert gray (2fe) | Light melon yellow (3ea) | None |

(3) Utilization of Various Carbon Sources

Various carbon sources were added to Pridham-Gottlieb agar and cultured at 28° C. for 2 weeks. The growth of the strain is shown in Table 6.

TABLE 6

| D-glucose | + | inositol | − |
|---|---|---|---|
| L-arabinose | + | L-rhamnose | + |
| D-xylose | + | D-mannitol | + |
| D-fructose | + | raffinose | − |
| sucrose | − | | |

(+: positive, −: negative)

(4) Various Physiological Properties

Various physiological properties of the present strain are as follows.

(a) Range of growth temperature (yeast extract-malt extract agar, incubation for 2 weeks) 15° C. to 41° C.
(b) Range of optimum growth temperature (yeast extract-malt extract agar, incubation for 2 weeks) 20° C. to 37° C.
(c) Liquefaction of gelatin (glucose-peptone-gelatin medium) positive
(d) Coagulation of milk (skim milk medium) positive
(e) Peptonization of milk (skim milk medium) positive
(f) Hydrolysis of starch (inorganic salts-starch agar) positive
(g) Formation of melanoid pigment (peptone-yeast extract-iron agar) positive, (tyrosine agar) negative
(h) Production of hydrogen sulfide (peptone-yeast extract-iron agar) positive
(i) Reduction of nitrate (broth containing 0.1% potassium nitrate) negative
(j) Sodium chloride tolerance (yeast extract-malt extract agar, incubation for 2 weeks) grown at a salt content of 7% or less (5) Chemotaxonomy LL-diaminopimelic acid was detected from the cell wall of the present strain.

From the above-mentioned microbial characteristics, the present inventors determined that the present strain belongs to the genus *Streptomyces*.

(The Taxonomical Properties of A-1545 Strain)

(1) Morphological Characteristics

Rectiflexibiles type aerial hyphae were extended from vegetative hyphae in this strain. Spore chains consisting of about 50 of spores were formed at the end of the matured aerial hyphae. The size of the spores was about 0.8×1.0 μm, the surface of the spores was smooth, and specific organs such as sporangium, sclerotium and flagellum were not observed.

(2) Cultural Characteristics on Various Media

Cultural characteristics of the strain after incubation at 28° C. for two weeks on various media are shown in Table 7. The color tone is described by the color names and codes which are shown in the parentheses of Tresner's Color wheels.

TABLE 7

| Medium | Growth | Aerial hyphae | Color of vegetative hyphae | Soluble pigment |
|---|---|---|---|---|
| Yeast extract - malt extract agar (ISP-2) | Good | Abundant Grayish yellowish pink (5cb) | Light melon yellow–Nude tan (3ea–4gc) | None |
| Oatmeal agar (ISP-3) | Moderate | Thin Grayish yellowish pink (5cb) | Pearl pink (3ca) | None |
| Inorganic salts - starch agar (ISP-4) | Good | Thin Grayish yellowish pink (5cb) | Light Ivory (2ca) | None |
| Glycerol - asparagine agar (ISP-5) | Good | Abundant Grayish yellowish pink (5cb) | Pearl pink (3ca) | None |
| Peptone-yeast extract - iron agar (ISP-6) | Moderate | None | Light melon yellow (3ea) | None |
| Tyrosine agar (ISP-7) | Good | Abundant Grayish yellowish pink (5cb) | Light melon yellow (3ea) | None |

(3) Utilization of Various Carbon Sources

Various carbon sources were added to Pridham-Gottlieb agar and cultured at 28° C. for 2 weeks. The growth of the strain is shown in Table 8.

TABLE 8

| D-glucose | + | inositol | ± |
|---|---|---|---|
| L-arabinose | + | L-rhamnose | + |
| D-xylose | + | D-mannitol | + |
| D-fructose | + | raffinose | + |
| sucrose | − | | |

(+: positive, ±: slightly positive, −: negative)

(4) Various Physiological Properties

Various physiological properties of the present strain are as follows.

(a) Range of growth temperature (yeast extract-malt extract agar, incubation for 2 weeks) 10° C. to 37° C.
(b) Range of optimum growth temperature (yeast extract-malt extract agar, incubation for 2 weeks) 20° C. to 33° C.
(c) Liquefaction of gelatin (glucose-peptone-gelatin medium) negative
(d) Coagulation of milk (skim milk medium) positive
(e) Peptonization of milk (skim milk medium) positive (f) Hydrolysis of starch (inorganic salts-starch agar) positive
(g) Formation of melanoid pigment (peptone-yeast extract-iron agar) negative, (tyrosine agar) negative
(h) Production of hydrogen sulfide (peptone-yeast extract-iron agar) positive
(i) Reduction of nitrate (broth containing 0.1% potassium nitrate) negative
(j) Sodium chloride tolerance (yeast extract-malt extract agar, incubation for 2 weeks) grown at a salt content of 7% or less (5) Chemotaxonomy LL-diaminopimelic acid was detected from the cell wall of the present strain.

From the above-mentioned microbial characteristics, the present inventors determined that the present strain belongs to the genus *Streptomyces*.

(The Taxonomical Properties of AB-1896 Strain)

(1) Morphological Characteristics

The AB-1896 strain showed good or moderate growth on the culture media used to identify the strain at 28° C. for 7 to 14 days. No hypha was observed during the cultures and one spore was observed on each vegetative hyphae. The spore had a sphere form and the size thereof was about 0.8 to 0.9 μm, and the surface of the spores was warty. Specific organs such as sporangium, sclerotium and flagellum were not observed.

(2) Cultural Characteristics on Various Media

Cultural characteristics of the strain after incubation at 28° C. for two weeks on various media are shown in Table 9. The color tone is described by the color names and codes which are shown in the parentheses of Tresner's Color wheels.

TABLE 9

| Medium | Growth | Color of vegetative hyphae | Soluble pigment |
|---|---|---|---|
| Yeast extract - malt extract agar (ISP-2) | Good | Bisque Berver (3li) (3ec) | None |
| Oatmeal agar (ISP-3) | Moderate Cork tan (4ie) | Light melon yellow (3ea) | None |
| Inorganic salts - starch agar (ISP-4) | Good Berver (3li) | Light melon yellow (3ea) | None |
| Glycerol - asparagine agar (ISP-5) | Moderate Light olive drab (1li) | Pearl pink (3ca) | None |
| Peptone-yeast extract - iron agar (ISP-6) | Good Berver (3li) | Light melon yellow (3ea) | None |
| Tyrosine agar (ISP-7) | Moderate Light olive gray (1½ge) | Pearl pink (3ca) | None |

(3) Utilization of Various Carbon Sources

Various carbon sources were added to Pridham-Gottlieb agar and cultured at 28° C. for 2 weeks. The growth of the strain is shown in Table 10.

TABLE 10

| D-glucose | + | inositol | − |
|---|---|---|---|
| L-arabinose | + | L-rhamnose | − |
| D-xylose | + | D-mannitol | − |
| D-fructose | + | raffinose | + |
| sucrose | + | | |

(+: positive, −: negative)

(4) Various Physiological Properties

Various physiological properties of the present strain are as follows.

(a) Range of growth temperature (yeast extract-malt extract agar, incubation for 2 weeks) 20° C. to 41° C.
(b) Range of optimum growth temperature (yeast extract-malt extract agar, incubation for 2 weeks) 25° C. to 37° C.
(c) Liquefaction of gelatin (glucose-peptone-gelatin medium) negative
(d) Coagulation of milk (skim milk medium) positive
(e) Peptonization of milk (skim milk medium) positive
(f) Hydrolysis of starch (inorganic salts-starch agar) positive
(g) Formation of melanoid pigment (peptone-yeast extract-iron agar) negative, (tyrosine agar) negative
(h) Production of hydrogen sulfide (peptone-yeast extract-iron agar) negative
(i) Reduction of nitrate (broth containing 0.1% potassium nitrate) positive
(j) Sodium chloride tolerance (yeast extract-malt extract agar, incubation for 2 weeks) not grown at a salt content of 4%

(5) Chemotaxonomy

Meso-type diaminopimelic acid was detected from the cell wall of the AB-1896 strain. As major structural sugars of whole mycelia, xylose and mannose were detected. The type of acyl inpeptide glycan of the cell wall was a glycolyl type. Mycolic acid was not detected. As major menaquinone components, MK-9($H_4$), MK-9($H_6$), MK-10($H_4$) and MK-10($H_6$) were detected.

(6) Analysis of the 16S rRNA Gene

A culture broth of the AB-1896 strain was collected and then subjected to DNA extraction using Fast DNA kit (manufactured by Q-BIO gene). PCR was carried out in a reaction condition of 96° C./20 seconds, 50° C./20 seconds and 72° C./one minute in 30 cycles in total. As the primers, 9F(5'-GTGTTTGATCCTGGCTCAG-3') (sequence No. 11) and 536R (5'-GTATTACCGCGGCTGCTG-3') (sequence No. 12) were used. The PCR product was refined using a MinElute PCR Purification Kit (manufactured by QIAGEN) to provide a sequencing sample.

The sequencing was carried out using an ABI PRISM 310 Genetic Analyzer (manufactured by Applied Biosystems) and a BigDye Terminator kit according to their standard protocols. As the primers, 9F and 536R were used.

Thus obtained about 500 nucleotide sequenece on the 5' terminal side of the 16s rRNA gene of the present strain is described in the sequence no. 13.

The DNA sequences of known strains were obtained from Japan DNA Data Bank to examine the homology of 400 to 500 bases on the 5' terminal side of the 16s rRNA genes. As a result, this 16s rRNA gene had 98% homology with the 16s rRNA gene of *Micromonospora* sp. DSM44396 (GenBank, accession no. AJ560637), 98% homology with a gene of *Micromonospora* purpureochromogenes (GenBank accession No. X92611), 95% homology with a gene of M. Chalcea IFO12135 (GenBank, accession no. D85489) which is a type strain of genus *Micromonospora* and 95% homology with a gene of *Verrucosispora* gifhornensis (Gen Bank, accession no. Y15523) which is a type strain of genus *Verrucosispora*.

Although the AB-1896 strain had almost the same characteristics as the genus *Micromonospora*, it corresponded imperfectly to the genus *Micromonospora* in the point that arabinose was not detected but mannose was detected as the major structural sugar of the whole mycelia. Also, the AB-1896 strain did not correspond perfectly to the genus *Verrucosispora* in the point that the spores peculiar in *Verrucosispora gifhornensis* were not observed on the medium used to identify the strain. The present inventors of the present invention decided that the AB-1896 strain is actinomycetes belonging to the family Micromonosporaceae in consideration of the above taxonomical properties.

According to the present invention, first in the process (A), the macrolide compound 11107B which is starting material (substrate) is incubated in the presence of the above strains or products prepared by its cultured mycelia and further in the presence of oxygen. This treatment may be carried out by adding the substrate in the culture broth when culturing the above strains in an aerobic condition or, as the case may be, by adding the substrate in a suspension solution of the cultured mycelia of the above strains as it is or of a product prepared by homogenizing these cells with flowing gas containing oxygen, for example, air.

The substrate may be added to the culture broth before culturing or when a fixed time passes after the start of culturing. The above mycelia may be produced by inoculating any one of the above strains into a medium containing a nutrient and culturing aerobically. The culturing of the strain for producing mycelia preparations or the culturing of the strain which is carried out in the situation where the substrate is added may be performed according to a method of culturing general microorganisms fundamentally. However, in general, the culturing is preferably carried out in an aerobic condition by, for example, flask shaking culture and tank culture according to liquid culture.

As the medium used for culturing, any medium may be used insofar as it contains a nutrient which microorganisms belonging to the genus *Mortierella*, the genus *Streptomyces* or the family Micromonosporaceae can utilize, and various synthetic media, semi-synthetic media and natural media may be all utilized. As the medium composition, various carbon sources such as glucose, galactose, sucrose, maltose, fructose, glycerin, dextrin, starch, molasses and soybean oil may be used either independently or in combinations.

As the nitrogen source, there can be used a single or a combination of organic nitrogen sources such as pharma media, peptone, meat extract, soybean meal, fish meal, gluten meal, casein, dry yeast, aminoacid, yeast extract, NZ-caseandurea, and inorganic nitrogen sources such as sodium nitrate and ammonium sulfate. Additionally, for example, there can be added and used salts such as sodium chloride, potassium chloride, calcium carbonate, magnesium sulfate, sodium phosphate, potassium phosphate copper sulfate, iron sulfate, manganese chloride or cobalt chloride; heavy metal salts; vitamins such as vitamin B or biotin; and inclusion agents such as cyclodextrins, if necessary. Further, when foaming is remarkable during culture, various defoaming agents can be appropriately added in the medium as necessary. When the defoaming agent is added, it is required to set at a concentration for not adversely affecting the production of an objective substance.

The culture condition can be appropriately selected within the range at which the microbial strain grows well and can produce the above-mentioned substance. For example, the pH of a medium is about 5 to 9, and preferably nearby neutral in general. The temperature of fermentation is usually kept at 20° C. to 40° C. and preferably 24° C. to 30° C. The fermentation period is about 1 to 8 days, and usually about 2 to 5 days. The above-mentioned fermentation conditions can be suitably changed in accordance with the kind and property of microorganism used, external conditions and the like, and it is needless to say that an optimum condition can be selected.

Also, the culture mycelia preparation is prepared by suspending mycelia separated by centrifugation or filtration or homogenized in a proper solution after the culturing is finished. Examples of the solution used for the suspension of the mycelia include the above-mentioned medium or buffer solutions such as tris-acetic acid, tris-hydrochloric acid, sodium succinate, sodium citrate, sodium phosphate and potassium phosphate either singly or in combinations. The pH of the buffer solution is 5.0 to 9.0 and preferably 6.0 to 7.5.

The 11107B substance as the substrate may be added in a culture broth or a suspension solution of mycelia either as a powder as it is or as a solution dissolved in a water-soluble solvent, for example, ethanol, methanol, acetone or dimethylsulfoxide. The amount of the 11107B substance added is preferably 50 to 5000 mg per 1 L of the culture broth in the case of the culture broth. After the addition of the substrate, procedures such as flask shaking or tank culture are conducted at 20 to 40° C. for about 1 to 5 days to run a reaction in an aerobic condition, whereby the 11107B substance as the substrate can be converted into the 11107D substance.

Next, in the process (B), the target 11107D substance is recovered from the incubated solution obtained in the above process (A). Suitable methods are selected from various known purification methods which are usually used to isolate microorganism metabolites and used in combination to isolate the 11107D substance from the reaction mixture in the process (A). For example, extraction by an organic solvent such as methanol, ethanol, butanol, acetone, ethyl acetate, butyl acetate, chloroform or toluene; various kinds of ion-exchange chromatography; gel filtration chromatography using Sephadex LH-20; the treatment of adsorption and desorption by absorption chromatography using a hydrophobic adsorbing resin such as Diaion HP-20, active carbon or silica gel, or thin layer chromatography; or high-performance liquid chromatography using a reverse phase column and so on may be used independently or in combinations or used repeatedly whereby the 11107D substance can be separated and purified.

EXAMPLES

The present invention will be explained in more detail by way of Examples, which are not intended to limit the scope of the present invention. In the following Examples, all designations of % indicate weight percentage (wt.%), unless otherwise noted.

Referential Example 1

Production of 11107B Substance as Starting Material

One loopful of the slant culture (ISP-2 medium) of Streptomyces sp. Mer-11107 strain (FERM BP-7812) was inoculated into a 500 mL Erlenmeyer flask containing 50 mL of seed medium (2.0% of glucose, 1.0% of soybean meal (ESUSAN-MEAT manufactured by Ajinomoto Co. Ltd.), 0.5% of yeast extract (manufactured by Oriental Yeast Co., Ltd.), 0.25% of sodium chloride, 0.32% of calcium carbonate, pH 6.8 before sterilized), and it was cultured at 28° C. for two days to give the first seed culture broth. 0.1 mL of the culture broth was inoculated into a 500 mL Erlenmeyer flask containing 100 mL of the same seed medium and it was cultured at 28° C. for one day to give the second seed culture broth. The second seed culture broth (800 mL) thus obtained was inoculated into a 200 L tank containing 100 L of a production medium (5.0% of soluble starch, 0.8% of Pharmamedia, 0.8% of gluten meal, 0.5% of yeast extract and 0.1% of calcium carbonate, pH 6.8 before sterilized) and it was cultured for five days with the following conditions, to give a culture broth.

Culture temperature: 28° C.
Agitation: 90 rpm
Aeration: 1.0 vvm
Internal pressure: 20 kPa A part of the culture broth (10 L) thus obtained was extracted with 10 L of 1-butanol, and then the resulting butanol layer was evaporated to dryness, to give 100 g of crude active fraction. The crude active fraction was applied on Sephadex LH-20 (1500 mL; manufactured by Pharmacia Co. Ltd. ), and eluted with tetrahydrofuran-methanol (1:1) as a solvent. An eluted fraction from 540 mL to 660 mL was concentrated to dryness, to give a residue (660mg). The resulting residue was dissolved in a mixture of ethyl acetate and methanol (9:1; v/v) and subjected to silica gel column chromatography (WAKO GEL C-200, 50 g). The column was eluted with a mixture (2 L) consisting of n-hexane and ethyl acetate (1:9, v/v), the fractions eluted from 468 mL to 1260 mL were collected, evaporated to give 25 mg of a crude active fraction.

The obtained crude active fraction was subjected to preparative high performance liquid chromatography (HPLC) under the following preparative HPLC condition (A), and the fractions eluted at the retention time of 34 minutes were collected. After removing acetonitrile, the respective fractions were desalted by HPLC under the following preparative HPLC condition (B) to give 11107B (Retentiontime: 37 minutes, 6 mg).

Preparative HPLC Conditions A:
 Column: YMC-PACK ODS-AM SH-343-5AM, φ20 mm×250 mm (manufactured by YMC Co.)
 Temperature: room temperature
 Flow rate: 10 mL/min.
 Detection: 240 nm
 Eluent: acetonitrile/0.15% aqueous potassium dihydrogenphosphate (pH 3.5) (2:8 to 8:2, v/v, 0 to 50 min., linear gradient)

Preparative HPLC Conditions B:
 Column: YMC-PACK ODS-AM SH-343-5AM, φ20 mm×250 mm (manufactured by YMC Co.)
 Temperature: room temperature
 Flow rate: 10 mL/min.
 Detection: 240 nm
 Eluent:-methanol/water (2:8 to 10:0, v/v, 0 to 40 min., linear gradient)

Example 1

Isolation of AB-1704 Strain

One loopful of the slant culture (0.5% of soluble starch, 0.5% of glucose, 0.1% of fish meat extract (manufactured by Wako Pure Chemical Industries, Ltd.), 0.1% of yeast extract (manufactured by Oriental Yeast Co., Ltd.), 0.2% of NZ-case (manufacured by Humko Sheffield Chemical Co.), 0.2% of sodium chloride, 0.1% of calcium carbonate and 1.6% of agar (manufactured by Wako Pure Chemical Industries, Ltd.)) of the strain isolated from the soil was inoculated into a 65 mL test tube containing 7 mL of a seed medium (2.0% of soluble starch, 1.0% of glucose, 0.5% of polypeptone (manufactured by Nihon Pharmaceutical Co., Ltd.), 0.5% of yeast extract (manufactured by Oriental Yeast Co., Ltd.) and 0.1% of calcium carbonate), and it was cultured at 28° C. for three days in a rotary shaker to give a seed culture broth.

Further, 0.5 mL of the seed culture broth was inoculated into a 65 mL test tube containing 7 mL of a production medium (2.0% of soluble starch, 1.0% of glucose, 0.5% of polypeptone (manufactured by Nihon Pharmaceutical Co., Ltd.), 0.5% of yeast extract (manufactured by Oriental Yeast Co., Ltd.), and 0.1% of calcium carbonate), and it was cultured at 28° C. for three days in a rotary shaker. Next, a 25 mg/mL solution of the substrate 11107B substance in ethanol was prepared, and 0.2 mL of the solution was added to the culture. After addition, it was shaken at 28° C. for 48 hours to carry out conversion reaction. After the reaction, the reaction mixture was analyzed by HPLC under the following analytic HPLC condition (a), to give AB-1704 strain (FERM BP-8551) by which the 11107D substance was formed in the reaction-mixture.

Analytic HPLC Condition (a)
 Column: CAPCELL PAK C18 SG120 φ4.6 mm×250 mm (manufactured by SHISEIDO CO.,)
 Temperature: 40° C.
 Flow rate: 1 mL/min.
 Detection: 240 nm
 Eluent: acetonitrile/0.15% potassium dihydrogenphosphate (pH 3.5) (3:7 to 5:5, v/v, 0 to 18 minutes, linear gradient), acetonitrile/0.15% potassium dihydrogenphosphate (pH3.5) (5:5to85:15, v/v, 18to22minutes, linear gradient)
 Retention time: 11107D substance 9.9 min., 11107B substance 19.4 min.

Example 2

Isolation of A-1544 Strain and A-1545 Strain

One loopful of the slant culture (yeast-malt agar) of the strain isolated from the soil was inoculated into a 250 mL Erlenmeyer flask containing 20 mL of a seed medium (2.4% of soluble starch, 0.1% of glucose, 0.5% of soybean meal (ESUSAN-MEAT manufactured by Ajinomoto Co., Ltd.), 0.3% of beef extract (manufactured by Difco), 0.5% of yeast extract (manufactured by Difco), 0.5% of triptone-peptone (manufactured by Difco), and 0.4% of calcium carbonate), and it was cultured at 28° C. for three days in a rotary shaker to give a seed culture broth.

Further, 0.6 mL of the seed culture broth was inoculated into a 500 mL Erlenmeyer flask containing 60 mL of a production medium (2.0% of soluble starch, 2.0% of glucose, 2.0% of soybean meal (ESUSAN-MEAT manufactured by Ajinomoto Co., Ltd.), 0.5% of yeast extract (manufactured by Oriental Yeast Co., Ltd.), 0.25% of sodium chloride, 0.32% of calcium carbonate, 0.0005% of copper sulfate, 0.0005% of manganese chloride, 0.0005% of zinc sulfate, pH 7.4 before sterilization), and it was cultured at 28° C. for four days in a rotary shaker. Each 2 mL of the resulting culture was dispensed into 15 mL test tubes. Next, a 20 mg/mL solution of the substrate 11107B substance in dimethyl sulfoxide was prepared, and 0.05 mL of the solution was added. After the addition, it was shaken at 28° C. for 23 hours to carry out conversion. After the reaction, the reaction mixture was analyzed by HPLC under the following analytic HPLC condition (b) to give A-1544 strain (FERMBP-8446) and A-1545 strain (FERM BP-8447) by which the 11107D substance was formed in the reaction mixture.

Analytic HPLC Condition (b)
 Column: CAPCELLPAKC18 SG120 φ4.6 mm×250 mm (manufactured by SHISEIDO CO.,)
 Temperature: 40° C.
 Flow rate: 1 mL/min.
 Detection: 240 nm
 Eluent: acetonitrile/water (50:50, v/v) Isocratic Retention time: 11107B substance 7.2 min., 11107D substance 3.6 min.

Example 3

Conversion by AB-1704 Strain in a Flask Scale

One loopful of the slant culture (0.5% of soluble starch, 0.5% of glucose, 0.1% of fish meat extract (manufactured by Wako Pure Chemical Industries, Ltd.), 0.1% of yeast extract (manufactured by Oriental Yeast Co., Ltd.), 0.2% of NZ-case (manufacured by Humko Sheffield Chemical Co.), 0.2% of sodium chloride, 0.1% of calcium carbonate, and 1.6% of agar (manufactured by Wako Pure Chemical Industries, Ltd.)) of *Streptomyces* sp. AB-1704 strain (FERM BP-8551) isolated from the soil was inoculated into a 500 mL Erlenmeyer flask containing 100 mL of a seed medium (2.0% of soluble starch, 1.0% of glucose, 0.5% of polypeptone (manufactured by Nihon Pharmaceutical Co., Ltd.), 0.5% of yeast extract (manufactured by Oriental Yeast Co., Ltd.) and 0.1% of calcium carbonate), and it was cultured at 28° C. for three days on a rotary shaker to give a seed culture broth. Further, 2 mL of the seed culture broth was inoculated into each of 150 Erlenmeyer flasks having a capacity of 500 mL and containing 100 mL of a production medium (2.0% of soluble starch, 1.0% of glucose, 0.5% of polypeptone (manufactured by Nihon Pharmaceutical Co., Ltd.), 0.5% of yeast extract (manufactured by Oriental Yeast Co., Ltd.) and 0.1% of calcium carbonate), and it was cultured at 28° C. for two days on a rotary shaker.

A 20 mg/mL solution of the substrate 11107B substance in ethanol was prepared, and each 0.44 mL of the solution was added to the resulting culture (100 mL/500 mL Erlenmeyer flask, 150 flasks). After the addition, it was shaken at 28° C. for 9 hours to conduct conversion reaction. After the completion of the reaction, the cultures were collected and separated into the culture supernatant and the mycelia by centrifugation at 2700 rpm for 10 minutes. The mycelia was extracted with 5 L of methanol and filtered to give the methanol extract solution. This methanol extract solution was evaporated to remove methanol, combined with the culture supernatant and extracted with 10 L of ethyl acetate. The resulting ethyl acetate solution was evaporated to give 2090 mg of a crude active fraction. The crude active fraction was dissolved in 4 mL of a mixture of tetrahydrofuran-methanol (1:1, v/v) and 6 mL of a 50% aqueous solution of acetonitrile, subjected to ODS column chromatography (manufactured by YMC Co., ODS-AM 120-S50 φ3.6 cm×43 cm) and eluted with a 40% aqueous solution of acetonitrile. An eluted fraction from 336 mL to 408 mL was concentrated to dryness under reduced pressure to give 560 mg of the residue. Further, the residue was dissolved in 10 mL of a 50% aqueous methanol solution, subjected to ODS column chromatography (manufactured by YMC Co., ODS-AM 120-S50 φ3.6 cm×40 cm) and eluted with a 50% aqueous solution of methanol. An eluted fraction from 1344 mL to 1824 mL was concentrated to dryness under reduced pressure to give 252 mg of 11107D substance.
Example 4 Conversion by A-1545 strain in a flask scale One loopful of the slant culture (yeast-maltagar) of A-1545 strain (FERM BP-8447) was inoculated into a 250 mL Erlenmeyer flask containing 25 mL of a seed medium (2.0% of soluble starch, 2.0% of glucose, 2.0% of soybean meal (ESU-SAN-MEAT manufactured by Ajinomoto Co., Ltd.), 0.5% of yeast extract (manufactured by Difco), 0.25% of sodium chloride, and 0.32% of calcium carbonate, pH 7.4 before sterilized), and it was cultured at 28° C. for two days in a rotary shaker to give a seed culture broth. Each 0.75 mL of the broth was dispensed into 2 mL serum tubes (manufactured by Sumitomo Bakelite Co., Ltd.), and an equal amount of a 40% aqueous solution of glycerol was added. After stirring, it was frozen at −70° C. to give a frozen seed. The frozen seed was melted, 0.25 mL thereof was inoculated into a 250 mL Erlenmeyer flask containing 25 mL of a seed medium (2.0% of soluble starch, 2.0% of glucose, 2.0% of soybean meal (ESU-SAN-MEAT manufactured by Ajinomoto Co., Ltd.), 0.5% of yeast extract (manufactured by Oriental Yeast Co., Ltd.), 0.25% of sodium chloride and 0.32% of calcium carbonate, pH 7.4 before sterilized), and it was cultured at 28° C. for two days on a rotary shaker to give a seed culture broth. Further, the seed culture broth (0.5 mL) was inoculated into a 500 mL Erlenmeyer flask containing 100 mL of a production medium (2.0% of soluble starch, 2.0% of glucose, 2.0% of soybean meal (ESUSAN-MEAT manufactured by Ajinomoto Co., Ltd.), 0.5% of yeast extract (manufactured by Oriental Yeast Co., Ltd.), 0.25% of sodium chloride, and 0.32% of calcium carbonate, pH 7.4 before sterilized), and it was cultured at 28° C. for three days on a rotary shaker.

Each of the resulting culture broths (100 mL/500 mL Erlenmeyer flask, 10 flasks) was subjected to centrifugation at 3000 rpm for 10 minutes to collect microorganism cells, and the cells were suspended into 100 mL of a 50 mM phosphate buffer solution (pH 6.0). Next, a 100 mg/mL solution of the substrate 11107B substance in dimethyl sulfoxide was prepared, and each 1 mL of the solution was added. After the addition, it was shaken at 28° C. for 24 hours to conduct conversion reaction. After the completion of the reaction, the reaction solutions were collected and separated into the supernatant and the mycelia by centrifugation at 5000 rpm for 20 minutes. The supernatant was extracted with 1 L of ethyl acetate. The mycelia was extracted with 500 mL of methanol and then filtered to obtain a methanol extract. The methanol extract was evaporated to remove methanol and extracted with 1 L of ethyl acetate. Each of the ethyl acetate layers was washed with water, dried and dehydrated over anhydrous sodium sulfate, and the combined layers were evaporated to give 937 mg of a crude fraction. The crude fraction was subjected to silica gel column chromatography (Kiesel gel 60, 50 g) and eluted with 1200 mL of a mixture of ethyl acetate and n-hexane (90:10; v/v) to obtain 234 mg of a fraction containing the 11107D substance. The resulting active fraction was subjected to preparative high performance liquid chromatography (HPLC) under the following preparative HPLC condition (C), and the resulting eluate was analyzed by HPLC under the following analytic HPLC condition (c). The solvent was removed from the fraction containing the 11107D substance thus obtained, to give 80 mg of the 11107D substance.

Preparative HPLC Condition (C)
   Column: CAPCELL PAK C18 UG120 φ30 mm×250mm (manufactured by SHISEIDO Co.)
   Flow rate: 20 mL/min.
   Detection: 240 nm
   Eluent: acetonitrile/water (30:70, v/v) isocratic Analytic HPLC Condition (c)
   Column: CAPCELLPAKC18 SG120 φ4.6 mm×250 mm (manufactured by SHISEIDO Co.)
   Temperature: 40° C.
   Flow rate: 1 mL/min.
   Detection: 240 nm
   Eluent: acetonitrile/water (35:65, v/v) isocratic
   Retention time: 11107D substance 7.8 min.

Example 5

Conversion by A-1544 Strain in a Flask Scale

Each of cultures of A-1544 strain (FERMBP-8446) (100 mL/500 mL Erlenmeyer flask, 10 flasks) obtained by a similar method as described in Example 4 was subjected to centrifugation at 3000 rpm for 10 minutes to collect microorganism cells, and the cells were suspended into 100 mL of a 50 mM phosphate buffer solution (pH 6.0). Next, a 100 mg/mL solution of the substrate 11107B in dimethyl sulfoxide was prepared, and each 1 mL of the solution was added. After the addition, it was shaken at 28° C. for 24 hours to run a conversion reaction. After the completion of the reaction, the reaction solutions were collected and separated into the supernatant and the mycelia by centrifugation at 5000 rpm for 20 minutes. The supernatant was extracted with 1 L of ethyl acetate. The mycelia was extracted with 500 mL of acetone, and then filtered to give an acetone extract. The acetone extract solution was evaporated to remove acetone, and then the residue was extracted with 1 L of ethyl acetate. Each of the ethyl acetate layers was washed with water, dried and dehydrated over anhydrous sodium sulfate, and the combined layers were evaporated to give 945 mg of a crude fraction. The crude fraction was subjected to silica gel column chromatography (Kiesel gel 60, 50 g), eluted with 100 mL of a mixture of ethyl acetate and n-hexane (50:50; v/v), 200 mL of a mixture of ethyl acetate and n-hexane (75:25; v/v) and a mixture (600 mL) of ethyl acetate and n-hexane (90:10; v/v), to give 463mg of a fraction containing the 11107D substance. The resulting fraction was subjected to preparative high performance liquid chromatography (HPLC) under the preparative HPLC condition (C) described in Example 4 and the resulting eluate was analyzed by HPLC under the analytic HPLC condition (c) described in Example 4. The solvent was removed from the fraction containing 11107D substance thus obtained, to give 304 mg of the 11107D substance.

Example 6

Isolation of F-1529 Strain and F-1530 Strain

One loopful of the slant culture (potato dextrose agar) of the strain isolated from the soil was inoculated into a 250 mL Erlenmeyer flask containing 20 mL of a seed medium (2.0% of potato starch, 1.0% of glucose, 2.0% of a soybean meal (ESUSAN-MEAT manufactured by Ajinomoto Co., Ltd.), 0.1% of potassium dihydrogenphosphate and 0.05% of magnesium sulfate heptahydrate), and it was cultured at 25° C. for three days on a rotary shaker to give a seed culture broth. Further, 0.6 mL of the seed culture broth was inoculated into 500 mL Erlenmeyer flask containing 60 mL of a production medium (2.0% of potato starch, 1.0% of glucose, 2.0% of a soybean meal (ESUSAN-MEAT manufactured by Ajinomoto Co., Ltd.), 0.1% of potassium dihydrogenphosphate and 0.05% of magnesium sulfate heptahydrate), and it was cultured at 28° C. for four days on a rotary shaker. 2 mL of the resulting culture broth was dispensed in each of 15 mL test tubes. Each test tube was subjected to centrifugation at 3000 rpm for 5 minutes to collect microorganism cells and then suspended in 2 mL of a 50 mM phosphate buffer solution (pH 7.0). Then, a 20 mg/mL solution of the substrate 11107B substance in dimethyl sulfoxide was prepared, and 0.05 mL of the solution was added. After the addition, it was shaken at 28° C. for 23 hours to conduct a hydroxylation reaction. After the reaction, the reaction mixture was analyzed by HPLC under the analytic condition (c) described in Example 4 to give F-1529 strain (FERM BP-8547) and F-1530 strain (FERM BP-8548) which both had the peak of the 11107D substance in HPLC.

Example 7

Conversion by F-1529 Strain in a Flask Scale

One loopful of the slant culture (potato dextrose agar) of *Mortierella* sp. F-1529 strain (FERM BP-8547) was inoculated into a 250 mL Erlenmeyer flask containing 25 mL of a seed medium (2.0% of potato starch, 1.0% of glucose, 2.0% of a soybean meal (ESUSAN-MEAT manufactured by Ajinomoto Co., Ltd.), 0.1% of potassium dihydrogenphosphate and 0.05% of magnesium sulfate heptahydrate), and it was cultured at 25° C. for two days on a rotary shaker to give a seed culture broth. Further, 0.6 mL of the seed culture broth was inoculated into each of a 500 mL Erlenmeyer flask containing 60 mL of a production medium (2.0% of potato starch, 1.0% of glucose, 2.0% of a soybean meal (ESUSAN-MEAT manufactured by Ajinomoto Co., Ltd.), 0.1% of potassium dihydrogenphosphate and 0.05% of magnesium sulfate heptahydrate), and it was cultured at 25° C. for three days on a rotary shaker.

Each resulting culture broth (60 mL/500 mL Erlenmeyer flask, 18 flasks) was subjected to centrifugation conducted out at 3000 rpm for 5 minutes to collect microorganism cells and then suspended in 60 mL of a 50 mM phosphate buffer solution (pH 7.0). Next, a 100 mg/mL solution of the substrate 11107B substance in dimethyl sulfoxide was prepared, and each 0.6 mL of the solution was added. After the addition, it was shaken at 25° C. for 22 hours to conduct conversion reaction. After the completion of the reaction, the culture broth was separated into the supernatant and the mycelia by centrifugation at 5000 rpm for 20 minutes. The supernatant was extracted with 1 L of ethyl acetate. The mycelia was extracted with 500 mL of acetone and filtered to give an acetone extract solution. The acetone extract solution was evaporated to remove acetone and then extracted with 1 L of ethyl acetate. The ethyl acetate layers were respectively washed with water, dehydrated and dried over anhydrous sodium sulfate and then combined with each other and evaporated, to give 1.21 g of a crude fraction including the 11107D substance. The crude fraction including the 11107D substance was subjected to silica gel column chromatography (Kiesel gel 60, 50 g), eluted with 1200 mL of a mixture of ethyl acetate and n-hexane (90:10; v/v), to give 369 mg of a fraction containing the 11107D substance.

The resulting fraction was subjected to preparative high performance liquid chromatography (HPLC) under the preparative HPLC condition (C) described in Example 4 to give an eluted fraction containing the 11107D substance. Then, the solvent was removed to give 180 mg of the 11107D substance.

Example 8

Conversion by F-1530 Strain in a Flask Scale

One loopful of the slant culture (potato dextrose agar) of *Mortierella* sp. F-1530 strain (FERM BP-8548) was inoculated into a 250 mL Erlenmeyer flask containing 25 mL of a seed medium (2.0% of potato starch, 1.0% of glucose, 2.0% of a soybean meal (ESUSAN-MEAT manufactured by Ajinomoto Co., Ltd.), 0.1% of potassium dihydrogenphosphate and 0.05% of magnesium sulfate heptahydrate), and it was cultured at 25° C. for two days on a rotary shaker to give a seed culture broth. Further, 0.6 mL of the seed culture broth was inoculated into a 500 mL Erlenmeyer flask containing 60 mL of a production medium (2.0% of potato starch, 1.0% of glucose, 2.0% of a soybean meal (ESUSAN-MEAT manufactured by Ajinomoto Co., Ltd.), 0.1% of potassium dihydrogenphosphate and 0.05% of magnesium sulfate heptahydrate), and it was cultured at 25° C. for three days on a rotary shaker.

Each obtained culture broth (60 mL/500 mL Erlenmeyer flask, 18 flasks) was subjected to centrifugation conducted at 3000 rpm for 5 minutes to collect microorganism cells and then suspended in 60 mL of a 50 mM phosphate buffer solution (pH 7.0). Next, a 100 mg/mL solution of the substrate 11107B substance in dimethyl sulfoxide was prepared, and each 0.6 mL of the solution was added. After the addition, it was shaken at 25° C. for 22 hours to conduct conversion reaction. After the completion of the reaction, the culture broth was separated into the supernatant and the mycelia by centrifugation at 5000 rpm for 20 minutes. The supernatant was extracted with 1 L of ethyl acetate. The mycelia was extracted with 500 mL of acetone and filtered to give an acetone extract solution. The acetone extract solution was evaporated to remove acetone and then extracted with 1 L of ethyl acetate. The ethyl acetate layers were respectively washed with water, dehydrated and dried using anhydrous sodium sulfate and then combined with each other and evaporated to give 0.89 g of a crude fraction including the 11107D substance. The crude fraction including the 11107D substance was subjected to silica gel column chromatography (Kiesel gel 60, 50 g), eluted with 1200 mL of a mixture of ethyl acetate and n-hexane (90:10; v/v) and then with 500 mL of ethyl acetate, to give 163mg of a crude fraction containing the 11107D substance. The resulting fraction was subjected to preparative high performance liquid chromatography (HPLC) under the HPLC condition (C) described in Example4 to give an eluted fraction containing the 11107D substance. Then, the solvent was removed to give 30 mg of the 11107D substance.

Example 9 Isolation of AB-1896 Strain

One loopful of the slant culture (0.5% of soluble starch, 0.5% of glucose, 0.1% of fish meat extract (manufactured by Wako Pure Chemical Industries, Ltd.), 0.1% of yeast extract (manufactured by Oriental Yeast Co., Ltd.), 0.2% of NZ-case (manufactured by Humko Sheffield Chemical Co.), 0.2% of sodium chloride, 0.1% of calcium carbonate, and 1.6% of agar (manufactured by Wako Pure Chemical Industries, Ltd.)) of the strain isolated from the soil was inoculated into a 65 mL test tube containing 5 mL of a seed medium (2.0% of soluble starch, 1.0% of glucose, 0.5% of polypeptone (manufactured by Nihon Pharmaceutical Co., Ltd.), 0.5% of yeast extract (manufactured by Oriental Yeast Co., Ltd.), and 0.1% of calcium carbonate), and it was cultured at 28° C. for ten days in a rotary shaker to give a seed culture broth. Further, 0.1 mL of the seed culture broth was inoculated into a 65 mL test tube containing 5 mL of a production medium (2.0% of soluble starch, 1.0% of glucose, 0.5% of polypeptone (manufactured by Nihon Pharmaceutical Co., Ltd.), 0.5% of yeast extract (manufactured by Oriental Yeast Co., Ltd.), and 0.1% of calcium carbonate), and it was cultured at 28° C. for three days in a rotary shaker. Next, a 40 mg/mL solution of the substrate 11107B substance in ethanol was prepared, and 0.05 mL of the solution was added to the culture. After addition, it was shaken at 28° C. for 24 hours to carry out hydroxylation reaction. After the reaction, the culture broth was subjected to HPLC analysis according to the following analytic condition (d) to give AB-1896 strain by which the 11107D substance was formed.

Analytic HPLC Condition (d)
Column: UNISON UK-C18, $\phi$4.6 mm×50 mm (manufactured by Imtakt)
Temperature: 30° C.
Flow rate: 2 mL/min.
Detection: 240 nm
Eluent: water/acetonitrile/formic acid (1000:10:1 to 10:1000:1, v/v/v, 0 to 4 minutes, linear gradient)
Retention time: 11107D substance 2.5 min.

Example 10

Conversion by AB-1896 Strain in a Test-Tube Scale

One loopful of the slant culture (0.5% of soluble starch, 0.5% of glucose, 0.1% of fish meat extract (manufactured by Wako Pure Chemical Industries, Ltd.), 0.1% of yeast extract (manufactured by Oriental Yeast Co., Ltd.), 0.2% of NZ-case (manufacured by Humko Sheffield Chemical Co.), 0.2% of sodium chloride, 0.1% of calcium carbonate, and 1.6% of agar (manufactured by Wako Pure Chemical Industries, Ltd.)) of AB-1896 strain was inoculated into a 65 mL test tube containing 5 mL of a seed medium (2.0% of soluble starch, 1.0% of glucose, 0.5% of polypeptone (manufactured by Nihon Pharmaceutical Co., Ltd.), 0.5% of yeast extract (manufactured by Oriental Yeast Co., Ltd.) and 0.1% of calcium carbonate), and it was cultured at 28° C. for 10 days on a rotary shaker to give a seed culture broth. Further, 0.1 mL of the seed culture broth was inoculated into a 65 mL test tube containing 5 mL of a production medium (2.0% of soluble starch, 1.0% of glucose, 0.5% of polypeptone (manufactured by Nihon Pharmaceutical Co., Ltd.), 0.5% of yeast extract (manufactured by Oriental Yeast Co., Ltd.), and 0.1% of calcium carbonate), and it was cultured at 28° C. for three days in a rotary shaker.

A 40 mg/mL solution of the substrate 11107B substance in ethanol was prepared, and 0.05 mL of the solution was added to the resulting culture broth (5 mL/65 mL test tube). After addition, it was shaken at 28° C. for 24 hours to carry out hydroxylation reaction. 3 mL of the resulting culture broth was separately collected, 2 mL of 1-butanol was added thereto, shaken, and then centrifuged at 3000 rpm for 10 minutes. The resulting supernatant was removed, to prepare a 2mL of methanol solution of the residue. It was subjected to HPLC analysis according to the following analytic conditions (e) and (f) to confirm that the 11107D substance was formed in the reaction mixture.

Analytic HPLC Condition (e)
Column: UNISON UK-Cl8, $\phi$4.6 mm×50 mm (manufactured by Imtakt)
Temperature: 40° C.
Flow rate: 2 mL/min.
Detection: 240 nm
Eluent: acetonitrile/0.01% trifluoroacetic acid (2:8 to 5:5, v/v, 0 to 10 minutes, linear gradient)
Retention time: 11107D substance 6.1 min.

Analytic HPLC Condition (f)
Column: UNISON UK-C18, $\phi$4.6 mm×50 mm (manufactured by Imtakt)
Temperature: 40° C.
Flow rate: 2 mL/min.
Detection: 240 nm
Eluent: methanol/0.01% trifluoroacetic acid (4:6 to 7:3, v/v, 0 to 10 minutes, linear gradient)
Retention time: 11107D substance 6.1 min.

The invention claimed is:

1. A method of producing the macrolide compound 11107D represented by the formula (II):

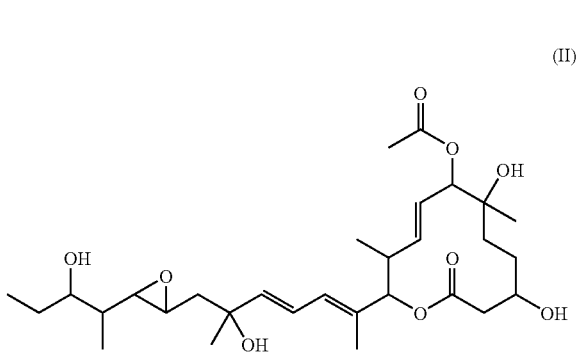

by a biological transformation method, wherein said method of producing the macrolide compound 11107D comprises the steps of:

providing the macrolide compound 11107B represented by the formula (I):

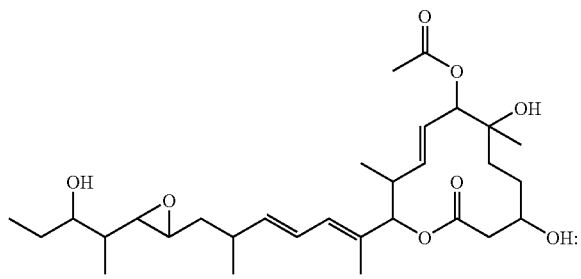

mixing the macrolide compound 11107B represented by the formula (I) with a strain having an ability of conducting the above-mentioned biological transformation method and belonging to the genus *Mortierella*, the genus *Streptomyces* or the family Micromonosporaceae or a preparation of its cultured mycelia;

incubating the mixture obtained in the preceding mixing step; and collecting the macrolide compound 11107D represented by the formula (II) from the incubated solution obtained in the preceding incubating step.

2. The production method according to claim 1, wherein the strain belonging to the genus *Streptomyces* is *Streptomyces* sp. AB-1704 strain (FERM BP-8551), A-1544 strain (FERM BP-8446) or A-1545 strain (FERM BP-8447).

3. An isolated or purified culture of *Streptomyces* sp. AB-1704 strain (FERM BP-8551) having the ability of transforming the macrolide compound 11107B represented by formula (I)

into the macrolide compound 11107D represented by formula (II)

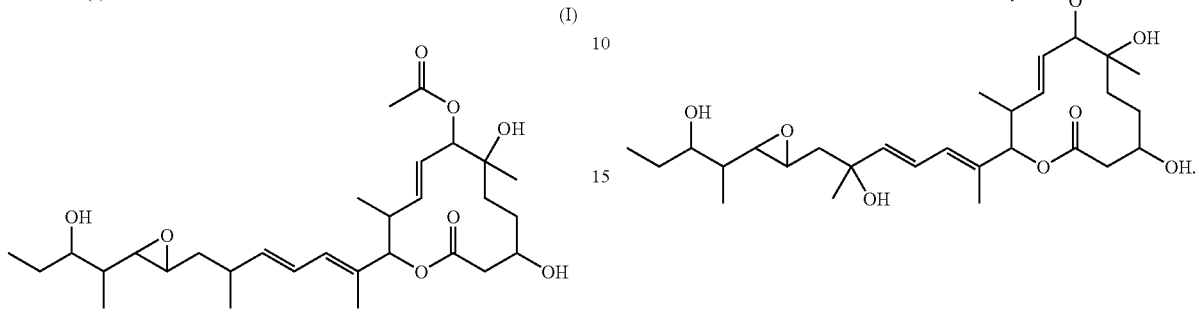

* * * * *

SEQUENCE LISTING

<160> NUMBER OF SEQ ID NOS: 13

<210> SEQ ID NO 1
<211> LENGTH: 18
<212> TYPE: DNA
<213> ORGANISM: Artificial Sequence
<220> FEATURE:
<223> OTHER INFORMATION: NS1 forward primer used to determine nucleotide
      sequence of 18s rRNA gene

<400> SEQUENCE: 1
gtagtcatat gcttgtct                                                  18

<210> SEQ ID NO 2
<211> LENGTH: 21
<212> TYPE: DNA
<213> ORGANISM: Artificial Sequence
<220> FEATURE:
<223> OTHER INFORMATION: NS3 forward primer used to determine nucleotide
      sequence of 18s rRNA gene

<400> SEQUENCE: 2
gcaagtctgg tgccagcagc c                                              21

<210> SEQ ID NO 3
<211> LENGTH: 22
<212> TYPE: DNA
<213> ORGANISM: Artificial Sequence
<220> FEATURE:
<223> OTHER INFORMATION: NS5 forward primer used to determine nucleotide
      sequence of 18s rRNA gene

<400> SEQUENCE: 3
aacttaaagg aattgacgga ag                                             22

<210> SEQ ID NO 4
<211> LENGTH: 23
<212> TYPE: DNA
<213> ORGANISM: Artificial Sequence
<220> FEATURE:
<223> OTHER INFORMATION: NS7 forward primer used to determine nucleotide
      sequence of 18s rRNA gene

<400> SEQUENCE: 4
gaggcaataa caggtctgtg atg                                            23

<210> SEQ ID NO 5
<211> LENGTH: 21
<212> TYPE: DNA
<213> ORGANISM: Artificial Sequence
<220> FEATURE:
<223> OTHER INFORMATION: NS2 reverse primer used to determine nucleotide
      sequence of 18s rRNA gene

<400> SEQUENCE: 5
cgttcagacc acggtcgtcg g                                              21

<210> SEQ ID NO 6
<211> LENGTH: 22
<212> TYPE: DNA
<213> ORGANISM: Artificial Sequence
<220> FEATURE:
<223> OTHER INFORMATION: NS4 reverse primer used to determine nucleotide
      sequence of 18s rRNA gene

<400> SEQUENCE: 6

-continued ttgaatttcc ttaactgcct tc                                            22

<210> SEQ ID NO 7
<211> LENGTH: 23
<212> TYPE: DNA
<213> ORGANISM: Artificial Sequence
<220> FEATURE:
<223> OTHER INFORMATION: NS6 reverse primer used to determine nucleotide
      sequence of 18s rRNA gene

<400> SEQUENCE: 7
ctccgttatt gtccagacac tac                                           23

<210> SEQ ID NO 8
<211> LENGTH: 20
<212> TYPE: DNA
<213> ORGANISM: Artificial Sequence
<220> FEATURE:
<223> OTHER INFORMATION: NS8 reverse primer used to determine nucleotide
      sequence of 18s rRNA gene

<400> SEQUENCE: 8
aggcatccac ttggacgcct                                               20

<210> SEQ ID NO 9
<211> LENGTH: 1733
<212> TYPE: DNA
<213> ORGANISM: Mortierella sp. F-1529

<400> SEQUENCE: 9
aaagattaag ccatgcatgt ctaagtataa acaactttgt actgtgaaac tgcgaatggc    60
tcattaaatc agttatagtt tatttgatta taccttacta cttggataac cgtggtaatt   120
ctagagctaa tacatgctaa aaatcccgac ttctggaagg gatgtattta ttagataaaa   180
aaccaatgcg ggcaaccgct tttctggtga ttcataataa cttttcgaat cgcatggcct   240
tgtgctagcg atgtttcatt caaatttctg ccctatcaac tttcgatggt aggatagagg   300
cctaccatgg ttttaacggg taacggggaa ttagggttcg attccggaga gggagcctga   360
gaaacggcta ccacatccaa ggaaggcagc aggcgcgcaa attacccaat cccgatacgg   420
ggaggtagtg acaataaata acaatacagg gctttatagt cttgtaattg gaatgagtac   480
aatttaaatc tcttaacgag gaacaattgg agggcaagtc tggtgccagc agccgcggta   540
attccagctc caatagcgta tattaaagtt gttgcagtta aaaagctcgt agttgaattt   600
taggtctggt tggacggtct gctctctagg gtttgtactg tcctgaccgg gccttacctt   660
ctggtgagct gtcgtgttgt ttactcagtc cggcagggaa ccaggacttt tactttgaaa   720
aaattagagt gtttaaagca ggcattcgct tgaatacatt agcatggaat aatagaatag   780
gactttggtt ctattttgtt ggtttctagg accgaagtaa tgattaatag ggatagttgg   840
gggcattagt atttaattgt cagaggtgaa attcttggat ttattaaaga ctaacttctg   900
cgaaagcatt tgccaaggat gttttcatta atcaagaacg aaagttaggg gatcgaagac   960
gatcagatac cgtcgtagtc ttaaccataa actatgccga ctagggatca ggcaggata   1020 ttttgacttg tttggcacct tatgagaaat caaagttttt gggttccggg gggagtatgg  1080
tcgcaaggct gaaacttaaa ggaattgacg gaagggcacc accaggagtg gagcctgcgg  1140
cttaatttga ctcaacacgg ggaaactcac caggtccaga catagtaagg attgacagat  1200
tgagagctct tcttgattc tatgggtggt ggtgcatggc cgttcttagt tggtggagtg   1260
atttgtctgg ttaattccgt taacgaacga gaccttaacc tgctaaatag ttaggtcaac  1320

-continued

```
gattgttgat cgtcaacttc ttagagggac tattgactat tagtcaatgg aagtttgagg      1380
caataacagg tctgtgatgc ccttagatgt tctgggccgc acgcgcgcta cactgatcaa      1440
gtcaacgagt ttacaacctt ggccggaagg tctgggtaat cttttgaaac ttgatcgtgc      1500
tggggatagt ccattgcaat tattggactt caacgaggaa ttcctagtaa gcgtgagtca      1560
tcagctcgcg ttgattacgt ccctgccctt tgtacacacc gcccgtcgct actaccgatt      1620
gaatggctta gtgaggcttt cggattggac tttggcagct ggcaacagca gctagggact      1680
gaaaagtcat ccaaacttgg tcatttagag gaagtaaaag tcgtaacaag gtt             1733
```

<210> SEQ ID NO 10
<211> LENGTH: 1731
<212> TYPE: DNA
<213> ORGANISM: Mortierella sp. F-1530

<400> SEQUENCE: 10

```
aaagattaag ccatgcatgt ctaagtataa acaactttgt actgtgaaac tgcgaatggc        60
tcattaaatc agttatagtt tatttgatta taccttacta cttggataac cgtggtaatt       120
ctagagctaa tacatgctaa aaatcccgac ttctggaagg gatgtattta ttagataaaa       180
aaccaatgcg ggcaaccgct tttctggtga ttcataataa cttttcgaat cgcatggcct       240
tgtgctagcg atgtttcatt caaatttctg ccctatcaac tttcgatggt aggatagagg       300
cctaccatgg ttttaacggg taacggggaa ttagggttcg attccggaga gggagcctga       360
gaaacggcta ccacatccaa ggaaggcagc aggcgcgcaa attacccaat cccgatacgg       420
ggaggtagtg acaataaata acaatacagg ctttatagt cttgtaattg gaatgagtac       480
aatttaaatc tcttaacgag gaacaattgg agggcaagtc tggtgccagc agccgcggta       540
attccagctc caatagcgta tattaaagtt gttgcagtta aaaagctcgt agttgaattt       600
taggcctggt tggacggtct gctctagggt ttgtactgtc ctgactgggt cttaccttct       660
ggtgagctgt cgtattgttt actcagtgcg gcagggaacc aggacttta ctttgaaaaa       720 attagagtgt ttaaagcagg cattcgcttg aatacattag catggaataa tagaatagga       780
ctttggttct attttgttgg tttctaggac cgaagtaatg attaataggg atagttgggg       840
gcattagtat ttaattgtca gaggtgaaat tcttggattt attaaagact aacttctgcg       900
aaagcatttg ccaaggatgt tttcattaat caagaacgaa agttagggga tcgaagacga       960
tcagataccg tcgtagtctt aaccataaac tatgccgact agggatcagg caaggatatt      1020
ttgacttgtt tggcacccta tgagaaatca agttttttgg gttccggggg gagtatggtc      1080
gcaaggctga aacttaaagg aattgacgga agggcaccac caggagtgga gcctgcggct      1140
taatttgact caacacgggg aaactcacca ggtccagaca tagtaaggat tgacagattg      1200
agagctcttt cttgattcta tgggtggtgg tgcatggccg ttcttagttg gtggagtgat      1260
ttgtctggtt aattccgtta acgaacgaga ccttaacctg ctaaatagtt aggccaacgt      1320
ttgttggtcg tcaacttctt agagggacta ttgactatta gtcaatggaa gtttgaggca      1380
ataacaggtc tgtgatgccc ttagatgttc tgggccgcac gcgcgctaca ctgatcaagt      1440
caacgagttt acaaccttgg ccggaaggtc tgggtaatct tttgaaactt gatcgtgctg      1500
gggatagtcc attgcaatta ttggacttca cgaggaatt cctagtaagc gtgagtcatc      1560
agctcgcgtt gattacgtcc ctgcccttg tacacaccgc ccgtcgctac taccgattga      1620
atggcttagt gaggctttcg gattggactt tggcagctgg caacagcagc tagggactaa      1680 aagtcatcc aaacttggtc atttagagga agtaaaagtc gtaacaaggt t               1731
```

```
<210> SEQ ID NO 11
<211> LENGTH: 19
<212> TYPE: DNA
<213> ORGANISM: Artificial Sequence
<220> FEATURE:
<223> OTHER INFORMATION: 9F primer used in the analysis of the 16S rRNA
      gene

<400> SEQUENCE: 11
gtgtttgatc ctggctcag                                                    19

<210> SEQ ID NO 12
<211> LENGTH: 18
<212> TYPE: DNA
<213> ORGANISM: Artificial Sequence
<220> FEATURE:
<223> OTHER INFORMATION: 536R primer used in the analysis of the 16S
      rRNA gene

<400> SEQUENCE: 12
gtattaccgc ggctgctg                                                     18

<210> SEQ ID NO 13
<211> LENGTH: 414
<212> TYPE: DNA
<213> ORGANISM: Micromonosporaceae AB-1896

<400> SEQUENCE: 13
gtcgagcgga aggcccttcg gggtactcga gcggcgaacg ggtgagtaac acgtgagcaa        60
cctgccctag gctttgggat aaccccggga aaccggggct aataccgaat atgacttctg       120
gtcgcatgac cggtggtgga aagttttttcg gcctgggatg ggctcgcggc ctatcagctt      180
gttggtgggg tgatggccta ccaaggcgac gacgggtagc cggcctgaga gggcgaccgg       240
ccacactggg actgagacac ggcccagact cctacgggag gcagcagtgg ggaatattgc       300
acaatgggcg gaagcctgat gcagcgacgc cgcgtgaggg atgacggcct tcgggttgta       360
aacctctttc agcagggacg aagcgtaagt gacggtacct gcagaagaag cgcc            414
```